(12) United States Patent
Chi et al.

(10) Patent No.: US 8,450,513 B2
(45) Date of Patent: *May 28, 2013

(54) SILANE COMPOSITIONS FOR POLYESTER NANOCOMPOSITES

(75) Inventors: Changzai Chi, Hockessin, DE (US); Gordon Mark Cohen, Wynnewood, PA (US); Surbhi Mahajan, Newark, DE (US); Anilkumar Raghavanpillai, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 326 days.

This patent is subject to a terminal disclaimer.

(21) Appl. No.: 12/846,913

(22) Filed: Jul. 30, 2010

(65) Prior Publication Data

US 2012/0029221 A1 Feb. 2, 2012

(51) Int. Cl.
  *C07F 7/18* (2006.01)
  *C09C 1/30* (2006.01)
  *C08K 9/06* (2006.01)

(52) U.S. Cl.
  USPC .......................................... 556/420; 556/414

(58) Field of Classification Search
  None
  See application file for complete search history.

(56) References Cited

U.S. PATENT DOCUMENTS

| | | | |
|---|---|---|---|
| 3,012,973 | A | 12/1961 | Atkins |
| 3,440,176 | A | 4/1969 | Sippel |
| 2004/0176600 | A1* | 9/2004 | Juhue et al. .................... 546/14 |
| 2004/0176660 | A1 | 9/2004 | Abe |
| 2009/0192254 | A1 | 7/2009 | Williamson et al. |
| 2011/0039990 | A1 | 2/2011 | Koch et al. |
| 2011/0048923 | A1 | 3/2011 | Nelson et al. |
| 2011/0077392 | A1 | 3/2011 | Baran, Jr. et al. |
| 2012/0029222 | A1* | 2/2012 | Chi et al. .................... 556/420 |

FOREIGN PATENT DOCUMENTS

JP 2002348148 A 12/2002

OTHER PUBLICATIONS

Konig, Susanne et al., Moderation of the electroosmotic flow in capillary electrophoresis by chemical modification of the capillary surface with tentacle-like oligourethanes, Journal of Chromatography A, 2000, pp. 79-88, vol. 894.

International Search Report dated Nov. 11, 2011, International Application No. PCT/US2011/045278.

Bergna, Horacio E., Colloidal silica: fundamentals and applications (Surfactant science series, v. 131), Horacio E. Bergna, William O. Roberts, eds., Colloid Chemistry of Silica: An Overview, 2006, pp. 9-35, Taylor & Francis Group, LLC, CRC Press.

East, Anthony J. et al., Kirk-Othmer Encyclopedia of Chemical Technology, Polyesters, Thermoplastic, 1996, pp. 609-653, vol. 19, John C. Wiley & Sons.

Knuf, Erin C. et al., Preparation of Discrete Oligoethers: Synthesis of Pentabutylene Glycol and Hexapropylene Glycol by Two Complementary Methods, Journal of Organic Chemistry, 2003, pp. 9166-9169, vol. 68, American Chemical Society.

Parvinzadeh, Mazeyar et al., Surface characterization of polyethylene terephthalate/silica nanocomposites, Applied Surface Science, 2010, pp. 2792-2802, vol. 256, Elsevier B.V.

Gurvich, S. M. et al., Synthesis of Some Monoalkyl Ethers of Polyethyleneglycol and Polypropyleneglycol, Translated from Zhurnal Organicheskoi Khimii, 1965, pp. 492-494, vol. 1, No. 3.

Yao, Xiayin et al., Interface structure of poly(ethylene terephthalate)/silica nanocomposites, Polymer 50, 2009, pp. 1251-1256, Elsevier Ltd.

\* cited by examiner

*Primary Examiner* — Yevegeny Valenrod

(57) ABSTRACT

Novel silane compositions have been prepared by reacting a 3-isocyanatopropyl trialkoxysilane with an alcohol or diol having a divalent alkylene or alkylene-ether group. The alcohol or diol has a formula weight less than about 5000. The compositions can be used to modify the surfaces of inorganic oxygen-containing materials, including but not limited to silica, silicates, borosilicates, aluminosilicates, days, and metal oxides. Surface treatment of silica nanoparticles with these compositions improves their improved dispersion in polyester nanocomposites.

4 Claims, 1 Drawing Sheet

SILANE COMPOSITIONS FOR POLYESTER NANOCOMPOSITES

CROSS-REFERENCE TO RELATED APPLICATIONS

Subject matter disclosed herein is disclosed and claimed in the following copending applications, filed contemporaneously herewith and assigned to the assignee of the present invention:

SURFACE-MODIFIED PARTICLES FOR POLYESTER NANOCOMPOSITES U.S. Publication No. 2012/00292222A1; and POLYESTER NANOCOMPOSITES U.S. Pat. No. 8,383,716.

FIELD OF THE INVENTION

The present disclosure relates to new silane compositions for use in forming polyester nanocomposites comprising silica nanoparticles and a polyester.

TECHNICAL BACKGROUND OF THE INVENTION

Nanocomposites are polymers reinforced with nanometer sized particles, i.e., particles with a dimension on the order of 1 to several hundred nanometers. When nanoparticles are dispersed homogeneously throughout the polymer matrix, dramatic improvements in properties such as strength, flexural and Young's modulus, heat distortion temperature, and barrier to gas permeation can observed at very low filler loadings (<10% by weight). The nature and degree of property improvements depend in part on the geometry of the nanoparticle, its surface chemistry, and its interaction with the polymer matrix. When the nanoparticles are not fully dispersed but are present as aggregates in the polymer matrix, the desired property improvement may not be fully realized.

There remains a need for methods for preparing polyester nanocomposites having high dispersion of nanoparticles.

SUMMARY OF THE INVENTION

In one embodiment of the invention described herein, a composition is provided described by Formula (I)

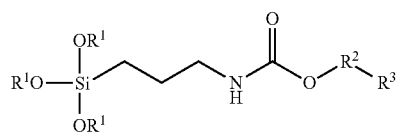

I wherein each $R^1$ is independently a $C_{1-4}$ alkyl group; $R^2$ is an alkylene or alkylene-ether group comprising at least three carbon atoms and having a formula weight less than about 5000; and $R^3$ is H, OH, or $CH_3$. In one embodiment, $R^2$ is the alkylene ether group $—(CH_2)_{(3+3n)}O_n—$,

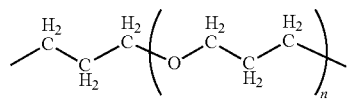

wherein n=0 to about 85, and $R^3$ is OH. This embodiment is described by Formula (II).

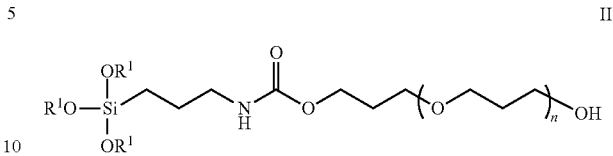

II

In another embodiment, a composition is provided comprising silica particles whose surface is modified with a Formula (II) compound wherein n=0 to 85.

In a further embodiment, a nanocomposite composition is provided comprising a polyester and silica nanoparticles whose surface is modified with a compound described by Formula (I) wherein n=0 to 5.

The invention further provides processes for preparing said compositions.

DETAILED DESCRIPTION OF THE INVENTION

Figure 1:
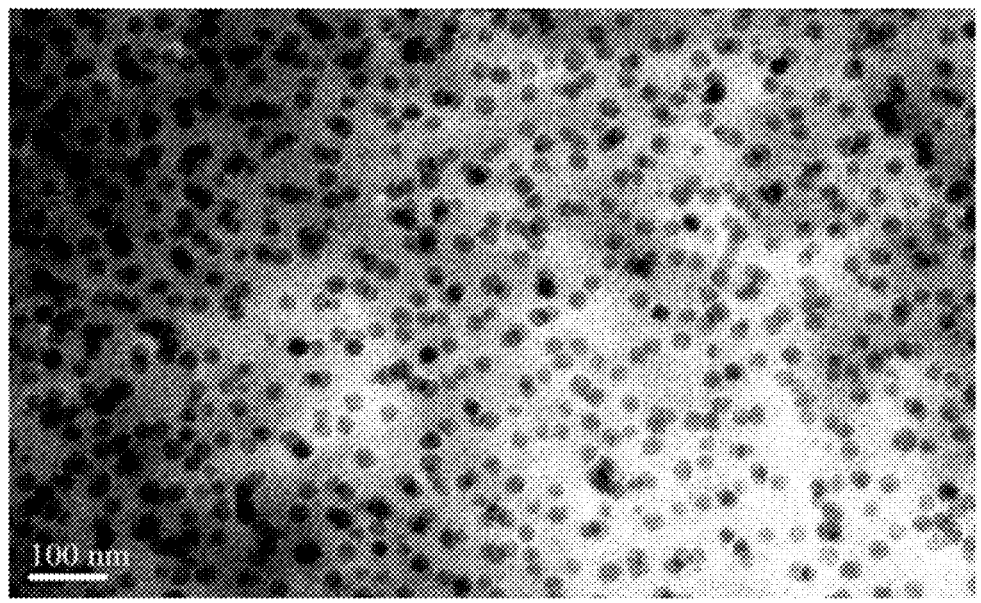
FIG. 1 is a transmission electron micrograph of a poly(propylene terephthalate) nanocomposite containing silica nanoparticles surface-modified with ICPTES-Polyol 3 (Example 3, Sample 3B), illustrating good nanoparticle dispersion.

In the context of this disclosure, a number of terms shall be utilized.

As used herein, the term "nanocomposite" or "polymer nanocomposite" means a polymeric material which contains particles, dispersed throughout the polymeric material, having at least one dimension in the 0.1 to 100 nm range ("nanoparticles"). The polymeric material in which the nanoparticles are dispersed is often referred to as the "polymer matrix." The term "polyester composite" refers to a nanocomposite in which the polymeric material includes at least one polyester.

As used herein, the term "alkyl" means a univalent group derived from an alkane by removing a hydrogen atom from any carbon atom:

—$C_nH_{2n+1}$ where $n \geq 1$.

As used herein, "an alkylene group" means the divalent group

—$C_nH_{2n}$— where $n \geq 1$.

As used herein, the term "alkylene-ether" means an alkylene group having at least one in-chain ether oxygen. One example is —$CH_2$—$CH_2$—O—. Another example is —$(CH_2)_{(3+3n)}O_n$—,

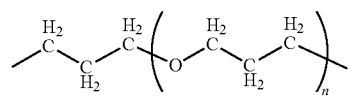

As used herein, "polyester" means a condensation polymer in which more than 50 percent of the groups connecting repeat units are ester groups. Thus polyesters may include polyesters, poly(ester-amides) and poly(ester-imides), so long as more than half of the connecting groups are ester groups. Preferably at least 70% of the connecting groups are esters, more preferably at least 90% of the connecting groups are ester, and especially preferably essentially all of the connecting groups are esters. The proportion of ester connecting groups can be estimated to a first approximation by the molar ratios of monomers used to make the polyester.

As used herein, "diol component" means a compound from which diol repeat units in the polyester are generated. For example, for poly(ethylene terephthalate), the diol component would be ethylene glycol.

As used herein, "acid component" means a compound from which acid repeat units in the polyester are generated. For example, for poly(ethylene terephthalate), the acid component would be terephthalic acid or dimethyl terephthalate.

Silanes

In one embodiment of the invention described herein, a composition is provided described by Formula (I)

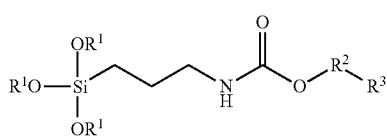

I wherein each $R^1$ is independently a $C_{1-4}$ alkyl group; $R^2$ is an alkylene or alkylene-ether group comprising at least one carbon atom and having a formula weight less than about 5000; and $R^3$ is H, OH, or $CH_3$. In some embodiments, the formula weight of $R^2$ is between and optionally including any two of the following values: 14 (i.e., when $R^2$ is —$CH_2$—), 100, 200, 300, 400, 500, 600, 700, 800, 900, 1000, 1200, 1500, 2000, 2500, 3000, 4000, and 5000.

The composition is prepared by reacting a compound described by Formula (III)

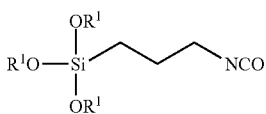

III (i.e., a 3-isocyanatopropyl trialkoxysilane, "ICPTAS") with HO—$R^2$—$R^3$. In an embodiment, HO—$R^2$—$R^3$ is the composition described by Formula (IV)

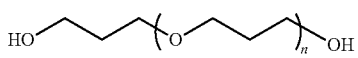

IV wherein n=0 to about 85. In some embodiments, n is between and optionally including any two of the following values: 0, 1, 2, 3, 4, 5, 6, 7, 8, 9, 10, 15, 20, 25, 35, 45, 55, 65, 75, and 85.

When HO—$R^2$—$R^3$ is the composition is described by Formula (IV), the product of its reaction with the ICPTAS is the composition described by Formula (II).

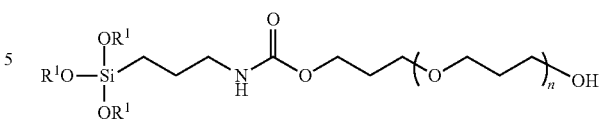

II

In one embodiment, the composition described by Formula (III) is

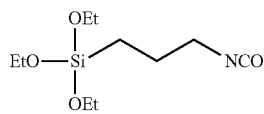

3-isocyanatopropyl triethoxysilane ("ICPTES"). ICPTES is available commercially, e.g., from Gelest, Inc. (Morrisville, Pa., USA).

When n=0, the Formula (IV) composition is 1,3-propanediol, which is available commercially, e.g., from Sigma-Aldrich (St. Louis, Mo., USA). When n is nonzero, Formula (IV) describes a "polyol" (i.e., a polyether diol) of 1,3-propanediol. Polyols of 1,3-propanediol with molecular weight from about 500 (n=7) to about 3000 are available commercially, e.g., from E. I. du Pont de Nemours & Co. (Wilmington, Del., USA), under the trade name DuPont™ Cerenol™ polyols. Polyols of 1,3-propanediol with lower molecular weight than 500 can be prepared by methods described in, e.g., E. C. Knuf et al. (*Journal of Organic Chemistry*, (2003), 68(23), 9166-9169) and S. M. Gurvich and R. Ya. Sokolova (*Zhurnal Organicheskoi Khimii*, (1965), 1(3), 500-502).

The reaction between the ICPTAS and HO—$R^2$—$R^3$ is carried out in the absence of oxygen in a nonprotic, anhydrous solvent in which it is sufficiently soluble, as indicated by the clarity of the mixture of HO—$R^2$—$R^3$ and solvent. For example, diethyl ether can be used as a solvent when HO—$R^2$—$R^3$ is the composition described by Formula (IV) wherein n=0 to about 16. The ICPTAS and HO—$R^2$—$R^3$ are reacted in a 1:1 to 1:1.2 molar ratio. In one embodiment, the reaction is carried out without a catalyst. In another embodiment, the reaction is carried out the presence of a catalyst such as dibutyltin dilaurate or a tertiary amine (e.g., triethylamine). Typically, the reaction is carried out under ambient conditions over several hours. In one embodiment, wherein HO—$R^2$—$R^3$ is the composition described by Formula (IV), the reaction temperature is about 0° C. to about 25° C. and the reaction time is about 4 hours to about 24 hours. The solvent is then removed by any convenient means, such as by applying a vacuum.

The silane compositions generally described by Formula (I) can be used to modify the surface characteristics of substrates onto which they are coated, particularly inorganic surfaces having hydroxyl groups that can be converted to stable oxane bonds by reaction with the silane. For example, they can be used to make a surface more hydrophobic. Thus, masonry can be rendered water repellent and glass surfaces of treated metal-glass capacitors can exhibit reduced electrical leakage in humid conditions. Laboratory glassware such as pipettes and graduated cylinders so treated can completely transfer aqueous solutions. Gas chromatography packing of diatomaceous earth or silica so treated can exhibit reduced tailing in use. The silane compositions materials generally described by Formula (I) can be utilized in composites, adhesives, sealants, and coatings. They can be used to modify the surfaces of inorganic oxygen-containing materials, including but not limited to silica, silicates, borosilicates, aluminosilicates, clays, and metal oxides.

In one embodiment, compositions described by Formula (II) wherein n=0 to 5 are used to modify the surfaces of silica nanoparticles, thereby improving the dispersion of such particles in polyester nanocomposites.

Silica Surface Modification

In an embodiment of the invention described herein, a composition is provided comprising silica particles whose surface is modified with a compound described by Formula (II) wherein each $R^1$ is independently a $C_{1-4}$ alkyl group; $R^2$ is an alkylene or alkylene-ether group comprising at least three carbon atoms and having a formula weight less than about 5000; and $R^3$ is H, OH, or $CH_3$. In one embodiment, each $R^1$ is independently ethyl or methyl, $R^2$ is the alkylene ether group $—(CH_2)_{(3+3n)}O_n—$, i.e.,

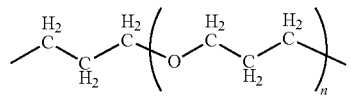

wherein n=0 to 5, and $R^3$ is OH. In one such embodiment, the silica particles are nanoparticles. In some embodiments, n is between (and optionally including) any two of the following values: 0, 1, 2, 3, 4, and 5.

The surface modified particles are prepared from an aqueous colloidal silica dispersion, which is an aqueous dispersion of amorphous silica particles having diameters of about 1 to about 150 nm. Preparation and properties of colloidal silica dispersions are described by H. E. Bergna in *Colloidal silica: fundamentals and applications (Surfactant science series, v. 131)*, H. E. Bergna and W. O. Roberts eds., CRC Press (1996), pp. 9-35. The $SiO_2$ concentration of suitable dispersions are typically about 15 to about 50 wt % $SiO_2$ in water and are commercially available, e.g., from W. R. Grace & Company (Columbia, Md., USA), Ondeo Nalco (Naperville, Ill., USA), and Sigma-Aldrich (St. Louis, Mo., USA). In some embodiments, the $SiO_2$ concentration is between (and optionally including) any two of the following values: 15, 20, 25, 30, 35, 40, 45, and 50.

The aqueous dispersion containing the silica nanoparticles is solvent exchanged with a diol or mixture of diols. In one embodiment, where the intended use of the particles is dispersion in a polyester to form a nanocomposite, the diol used can be the diol component of the polyester matrix, e.g., 1,3-propanediol ("PDO") for the polyester poly(propylene terephthalate); where the polyester is a blend (physical mixture) or copolymer (chemical mixture) of two or more polyesters, a mixture of the diol components of the polyesters can be used. Water is then removed from the dispersion by any convenient method, e.g., by boiling under vacuum.

The compound described by Formula (I) is then added to the colloidal silica/diol dispersion to form a mixture wherein the surface coverage of the silica particles is about 0.25 to about 4 molecules of Formula (I) compound per $nm^2$ silica particle surface. The amount of Formula (I) compound added to achieve this coverage will depend on silica particle size and geometry and the molecular weight of the Formula (I) compound. When the formula weight of $R^2$ in the Formula (I) compound is less than about 1000 and the silica particles are spherical nanoparticles, a typical amount is about 0.08 g to 0.15 g of Formula (I) compound per gram of silica.

The mixture is then heated at a temperature in the range from about 60° C. to about 215° C. for about 5 minutes to about 2 hours to react the Formula (I) compound with the silica surface; in one embodiment, the mixture is heated at about 100° C. for about 30 minutes. Optimum time and temperature for specific Formula (I) compounds and silica particles are readily determined by one having ordinary skill in the art.

Nanocomposites

In a further embodiment, a composition is provided comprising a polyester and silica nanoparticles dispersed therein, wherein the surface of the silica nanoparticles is modified with a compound described by Formula (I). The surface modification allows polyester nanocomposites to be prepared in which the nanoparticles are very well dispersed. In one embodiment, the polyester is poly(ethylene terephthalate) (PET), poly(ethylene isophthalate), poly(propylene terephthalate) (PPT), poly(butylene terephthalate) (PBT), a physical mixture of at least two of these; or a polyester copolymer whose diol component is at least two diols selected from ethylene glycol, 1,3-propane diol and 1,4-butanediol, and whose acid component is terephthalic acid (or, equivalently, dimethyl terephthalate) and/or isophthalic acid (or, equivalently, dimethyl isophthalate).

The nanocomposite is prepared by in situ polymerization, that is, polymerization of the polyester in the presence of a dispersion of the surface-treated silica nanoparticles in a diol or diol mixture corresponding to the diol component of the polymerized polyester. For example, to prepare a nanocomposite of PPT and silica nanoparticles, the silica nanoparticles would be introduced into the polymerization mixture as a dispersion in 1,3-propane diol. If the polyester is to be a copolymer, for example, of poly(butylene terephthalate) and poly(ethylene terephthalate), the silica nanoparticles would be introduced into the polymerization mixture as a dispersion in a mixture of 1,4-butanediol and ethylene glycol. Suitable methods of polyester polymerization are described in U.S. Published Patent Application 2009/0192254. which is hereby incorporated in its entirety for all purposes.

The polymerization process may be carried out in any way known in the art. For example it may be a batch, semibatch or continuous process. Both these types of processes are will known in the art; see A. J. East, et al. in the *Kirk-Othmer Encyclopedia of Chemical Technology*, John Wiley & Sons, J. I. Kroschwitz exec. ed., $4^{th}$ edition (1996), vol. 19, 609-653. For commercial use, a continuous process is preferred. Another process variation is melt polymerization of the polyester precursors to a polyester whose molecular weight is suitable for so-called solid state polymerization, and then subjecting this polyester to solid state polymerization to achieve the desired molecular weight.

Other materials may also optionally be present during the polymerization process, such as stabilizers, antioxidants, and other materials sometimes added to such processes. Other filler(s) and/or reinforcing agent(s) may also be present in the polymerization, either from the beginning of the process or added during the process as long as they do not interfere with the polymerization itself.

Figure 2:
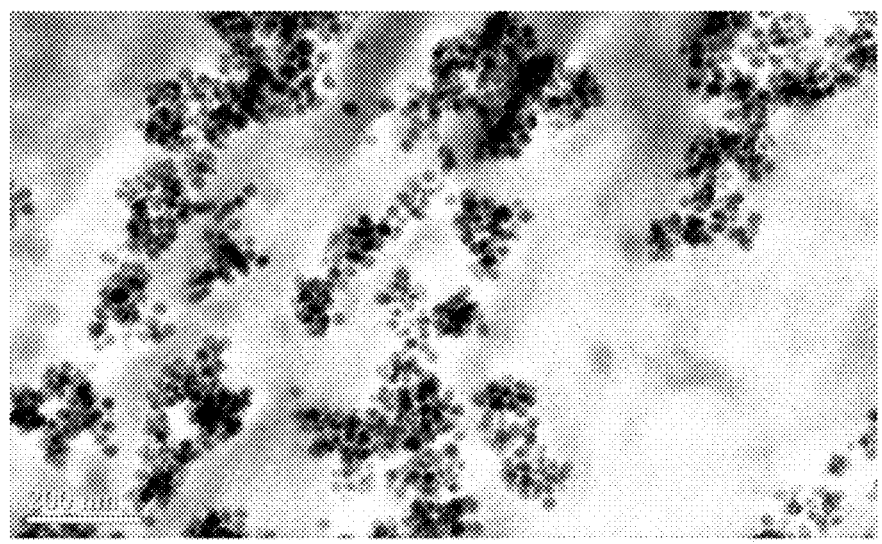
FIG. 2 is a transmission electron micrograph of a poly(propylene terephthalate) nanocomposite containing silica nanoparticles surface-modified with N-(3-triethoxysilylpropyl)-4-hydroxybutyramide (Comparative Example B), illustrating poor nanoparticles dispersion.

The polyester nanocomposites described herein are characterized by improved dispersion of silica nanoparticles throughout the polyester matrix in comparison with analogous compositions containing silica nanoparticles whose surfaces have not been modified with a compound described by Formula (I). This is illustrated in FIGS. 1 and 2. FIG. 1 is a transmission electron micrograph of a poly(propylene terephthalate) nanocomposite containing silica nanoparticles surface-modified with ICPTES-Polyol 3 (Example 3, Sample 3B) in accordance with the present invention, illustrating good nanoparticle dispersion. FIG. 2 is a transmission electron micrograph of a poly(propylene terephthalate) nanocomposite containing silica nanoparticles surface-modified with N-(3-triethoxysilylpropyl)-4-hydroxybutyramide (Comparative Example B), not according to the present invention, illustrating poor nanoparticle dispersion. The improved dispersion results in mechanical property improvement in molded samples and reduced haze in film.

Articles comprising the polyester nanocomposite compositions produced by the present invention may be prepared by any means known in the art, such as, but not limited to, methods of injection molding, extrusion, blow molding, thermoforming, fiber spinning, or film blowing. The polyester nanocomposite compositions may be the form of, for example, film, sheet, containers, membranes, laminates, pellets, coatings, foam, monofilament fiber and multifilament yarn. The polyester nanocomposite compositions may be blended with ingredients such as flame retardants, plasticizers, pigments, other polymers (for example, polycarbonate) various rubber tougheners, and the like as needed. Many suitable additives are described in U.S. Published Patent Application 2009/0192254. which is hereby incorporated in its entirety for all purposes.

The polyester nanocomposite materials produced as described herein can be used in articles of manufacture in a wide variety of applications, including without limitation articles for: electrical and electronic applications, such as electrical connectors, plugs, switches, keyboard components, printed circuit boards, electronic cabinets and housings such as personal computer housings, printer housings, peripheral housings, server housings, and small electric motor components; automotive applications, such as distributor caps, coilformers, rotors, windshield wiper arms, headlight mountings, and other fittings, fenders, fascia, hoods, tank flaps and other exterior parts and interior automotive panels; control panels, chassis (cases); exterior and interior panels for vehicles such as trains, tractors, lawn mower decks, trucks, snowmobiles, aircraft, and ships; decorative interior panels for buildings; furniture such as office and/or home chairs and tables; industrial machinery, for example in molded conveyor-belt links; medical devices, such as nasal sprays and nebulizers; home appliances, such as food mixers, hair dryers, coffee makers, washing machine tubs and exterior parts, appliance handles, interior and exterior refrigerator panels, dishwasher front and interior panels and toasters; power tool housings such as drills and saws; and a variety of other applications, such as fiberoptical cable buffer tubes, countertops, camera parts, telephones, cell phones, and related equipment.

Polyester monofilaments are used as reinforcements for rubber articles, fishing lines, toothbrush bristles, paintbrush bristles and the like, and in industrial applications such as tire cords, composites, belts, and textiles. In addition, woven fabrics produced from monofilaments are used, for example, in industrial belts and paper machine clothing. Multifilament yarns can be produced comprising the polyester composites described herein using any of the typical processes well known in the art for making multifilament polyester yarns. Monofilaments and multifilament yarns can be woven into textile fabrics, using known processes.

Where a range of numerical values is recited herein, unless otherwise stated, the range is intended to include the endpoints thereof, and all integers and fractions within the range. It is not intended that the scope of the invention be limited to the specific values recited when defining a range.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations is as follows: "BDO" means 1,4-butanediol, "DBTDL" means dibutyltin dilaurate, "DMA" means dynamic mechanical analysis, "g" means gram(s), "GPC" means gel permeation chromatography, "h" means hour(s), "ICPTES" means 3-isocyanatopropyl triethoxysilane, "ICPTMS" means 3-isocyanatopropyl trimethoxysilane "min" means minute(s), "mL" means milliliter(s), "$M_n$" means number average molecular weight, "MPa" means megapascal(s), "mtorr" means millitorr, "$M_w$" means number average molecular weight, "PBT" means poly(butylene terephthalate). "PDO" means 1,3-propanediol, "PPT" means poly(propylene terephthalate), "rpm" means revolutions per minute, "TEM" means transmission electron microscopy, "$T_g$" means glass transition temperature, "$T_m$" means melting temperature, "$T_{HC}$" means crystallization temperature from the melt, "wt %" means weight percent (age), "$\Delta H_C$" means heat of crystallization, and "μL" means microliter(s).

Methods

Transmission electron microscopy was used to assess dispersion quality.

Molecular weights were measured by gel permeation chromatography.

Thermal transitions (glass transition ($T_g$), melting temperature ($T_m$), and the crystallization temperature from the melt ($T_{HC}$) and percent crystallinity (by the heat of crystallization, $\Delta H_C$) were measured by differential scanning calorimetry.

Haze was measured by UV/visible spectrophotometry using ASTM D-1003, Procedure B (unidirectional illumination with diffuse viewing). The instrument used was Varian Cary 5000 uv/vis/nir spectrophotometer equipped with a DRA 2500 diffuse reflectance accessory (150 mm integrating sphere).

Tensile modulus, tensile strength, and elongation at break were determined on tensile bars conforming to ISO 527-1 titled "Plastics—Determination of tensile properties." Measurements were done at room temperature. Testing was carried out in accordance with ISO 527-1 specifications.

Storage modulus (flexural) at elevated temperature was determined by dynamic mechanical analysis (DMA).

Materials

LUDOX® TMA colloidal silica, 34 wt % suspension in water; 1,3-propanediol, (99.6+% purity); dimethylene terephthalate (99+% purity); and 1,4-butanediol (99% purity, Reagent plus grade) were purchased from Sigma-Aldrich® (St. Louis, Mo., USA).

3-Isocyanatopropyl triethoxysilane (95% purity), 3-isocyanatopropyl trimethoxysilane (95% purity), N-(3-triethoxysilylpropyl)-4-hydroxybutyramide, bis(2-hydroxyethy)-3-aminopropyl triethoxysilane (62% in ethanol), and aminopropyl triethoxysilane (99+% purity) were purchased from Gelest, Inc. (Morrisville, Pa., USA).

Tyzor ® TPT catalyst was obtained from E. I. du Pont de Nemours & Co., Inc. (Wilmington, Del., USA).

N-propanol (99.99% purity, OmniSolv® high purity solvent) was obtained from EMD Chemicals (Gibbstown, N.J., USA).

Samples of the polyether diol

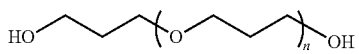

having molecular weight about 250 g/mol (n=3) and about 500 g/mol (n=7) were also obtained from the DuPont Company and are referred to herein as "Polyol 3" and "Polyol 7", respectively.

Example 1

Synthesis of Silanes 1,3-Propanediol (PDO), and 3-isocyanatopropyl triethoxysilane (ICPTES) were reacted in a 1:1 molar ratio to form ICPTES-PDO (Formula (II) wherein $R^1$ is ethyl and n is zero). Inside a nitrogen-filled glove box at ambient temperature, 3.05 g (0.04 mol) of PDO was added to a 250 mL round bottom flask with stirring bar. 40 mL of diethyl ether was added to the flask and the contents were stirred, forming a solution. To this solution was added 9.895 g (0.04 mol) of ICPTES slowly, followed by 76 µL ($1.2 \times 10^{-4}$ mol) of catalyst dibutyltin dilaurate (DBTDL). The reaction mixture was allowed to stir overnight. The next day, the solvent was stripped off in the glove box.

9.895 g (0.04 mol) ICPTES was similarly reacted with 0.04 mol of:

Polyol 3 to form ICPTES-Polyol 3 (Formula (II) wherein $R^1$ is ethyl and n is 3); and Polyol 7 to form ICPTES-Polyol 7 (Formula (II) wherein $R^1$ is ethyl and n is 7).

Similarly, 14.842 g (0.072 mol) 3-isocyanatopropyl trimethoxysilane (ICPTMS) was reacted with 0.06 mol of N-propanol to form ICPTMS-n-propanol (Formula (I) wherein $R^1$ is ethyl, $R^2$ is —$(CH_2)_2$— and $R^3$ is $CH_3$); and 0.06 mol of ICPTMS was reacted with 0.05 mol of 1,4-butanediol to form ICPTMS-BDO (Formula (I) wherein $R^1$ is ethyl, $R^2$ is —$(CH_2)_4$— and $R^3$ is OH).

Example 2

Colloidal Silica Solvent Exchange and Surface Modification 221.3 g aqueous colloidal silica dispersion (Ludox® TMA, 34 wt % silica) was mixed with 250 mL 1,3-propanediol (PDO). The water was boiled off from the mixture under vacuum. A transparent colloidal silica dispersion in PDO was obtained. 7.86 g ICPTES-PDO was then added to the colloidal silica PDO dispersion. The mixture was then heated at 100° C. for 30 min to react ICPTES-PDO onto the surface of silica nanoparticles.

The wt % of silica in the ICPTES-PDO treated silica PDO colloidal dispersion was measured to be 22.2 wt % by firing the sample at 600° C. for 12 hours. The amount of water in dispersion is 0.3144% measured by Karl Fisher titration.

This method was also used to prepare silica nanoparticles with the following surface treatments: ICPTES-Polyol 3, ICPTES-Polyol 7, ICPTMS-BDO, ICPTMS-n-propanol, bis (2-hydroxyethyl)-3-aminopropyl triethoxysilane, N-(3-triethoxysilylpropyl)-4-hydroxybutyramide, and ICPTES itself.

Example 3

Polymerization of PPT in the Presence of Surface Treated $SiO_2$

Dimethylterephthalate (134.17 g, 0.69 mol), 1,3-propanediol (68.46 g, 0.90 mol), and a colloidal dispersion of 22.2 wt % surface treated silica in PDO (33.78 g, surface treatment with ICPTES-PDO) prepared as in Example 2 were charged to a 500 mL three-necked round bottom flask. An overhead stirrer and a distillation condenser were attached. The reaction mass was kept under a $N_2$ purge atmosphere. The contents were degassed three times by evacuating down to 500 mtorr and refilling back with $N_2$ gas. The flask was immersed in a preheated metal bath set at 160° C. The solids were allowed to completely melt at 160° C. and the stirrer speed was slowly increased to 180 rpm. 67 µL of catalyst Tyzor®TPT was added under a $N_2$ blanket. The temperature was increased to 210° C. The system was maintained at 210° C. for 60 minutes to distill off most of the methanol produced. The temperature was increased to 250° C. and was held constant for 30 minutes. The nitrogen flush was closed off and vacuum ramp was started. After 36 min, the vacuum reached a value of 55 mtorr. The reaction was maintained under vacuum for approximately 41 min. Molecular weight, thermal analyses, and ash content of the nanocomposite thereby produced ("3A") are presented in Table 1.

PPT nanocomposites were similarly prepared using colloidal dispersions of silica nanoparticles that had been surface-treated with ICPTES-Polyol 3 (3B), ICPTES-Polyol 7 (3C), ICPTMS-BDO (3D), and ICPTMS-n-propanol (3E). Analyses of the nanocomposites thereby produced are presented in Table 1.

Comparative Example A

Polymerization of PPT in the Presence of $SiO_2$Articles without Surface Treatment Example 3 was repeated except that the silica particles had not been surface treated. Molecular weight, thermal analyses, and ash content of the nanocomposite thereby produced are presented in Table 1.

Comparative Example B

Polymerization of PPT in the Presence of $SiO_2$ Surface Treated with N-3-triethoxysilylpropyl)-4-hydroxybutyramide Dimethylterephthalate (134.17 g, 0.69 mol), 1,3-Propanediol (68.89 g, 0.90 mol) and 33.35 g of 22.5% colloidal surface treated silica in PDO (surface treatment with N-(3-triethoxysilylpropyl)-4-hydroxybutyramide) were charged to a 500 mL three necked round bottom flask. An overhead stirrer and a distillation condenser were attached. The reaction mass was kept under $N_2$ purge atmosphere. The contents were degassed three times by evacuating down to 500 mtorr and refilling back with $N_2$ gas. The flask was immersed in a preheated metal batch set at 160° C. The solids were allowed to completely melt at 160° C. and the stirrer speed was slowly increased to 180 rpm. 67 µL of catalyst Tyzor®TPT was added under a $N_2$ blanket. The temperature was increased to 210° C. The system was maintained at 210° C. for almost 2 hours to distill off most of the methanol produced. The temperature was increased to 250° C. and was held constant for 30 minutes. The nitrogen flush was closed off and vacuum ramp was started. After 29 min, the vacuum reached a value of 52 mtorr. The reaction was maintained under vacuum for approximately 1 h and 43 min. Molecular weight, thermal analyses, and ash content of the nanocomposite thereby produced are presented in Table 1.

Comparative Example C

Polymerization of PPT in the Presence of SiO$_2$ Surface Treated with bis(2-hydroxyethy)-3-aminopropyl triethoxysilane Example 3 was repeated except that the silica particles had been surface treated with bis(2-hydroxyethy)-3-aminopropyl triethoxysilane. Molecular weight, thermal analyses, and ash content of the nanocomposite thereby produced are presented in Table 1.

Comparative Example D

Polymerization of PPT in the Presence of SiO$_2$ Surface Treated with ICPTES Example 3 was repeated except that the silica particles had been surface treated with ICPTES. Particle dispersion as determined by TEM was poor (Table 2).

TABLE 1

| Sample | Ash (wt %) | $T_g$ (°C.) | $T_m$ (°C.) | $T_{HC}$ (°C.) | % Crystallinity as made, by $\Delta H_C$ | GPC analysis (g/mol) |
|---|---|---|---|---|---|---|
| Comp. Ex. A | 4.72 | 55 | 229 | 163 | 30.8 | $M_n$ = 24200, $M_w$ = 45800 |
| Comp. Ex. B | 5.25 | 53 | 229 | 167 | 30.6 | $M_n$ = 20600, $M_w$ = 44500 |
| Comp. Ex. C | 5.05 | 56 | 229 | 167 | 30.6 | $M_n$ = 20200, $M_w$ = 39000 |
| 3A | 4.92 | 53 | 228 | 166 | 32.7 | $M_n$ = 21300, $M_w$ = 45000 |
| 3B | 4.92 | 56 | 228 | 168 | 34.4 | $M_n$ = 24200, $M_w$ = 45800 |
| 3C | 5.00 | 54 | 229 | 168 | 33.9 | $M_n$ = 24200, $M_w$ = 45800 |

Example 4

Dispersion Quality of Silica in PPT Nanocomposites

Samples of the nanocomposites prepared in Example 3 and Comparative Examples A, B, and C were examined using transmission electron microscopy (TEM) to assess the quality of the dispersion of the silica particles. A representative example of "good" dispersion (Example 3B) is presented in FIG. 1. A representative example of "poor" dispersion (Comparative Example B) is presented in FIG. 2. Haze measurements were also used to assess dispersion quality of several samples, lower haze indicating better dispersion. Results are summarized in Table 2.

TABLE 2

| Sample | Silica Surface Treatment | Haze, % | Dispersion Quality by TEM |
|---|---|---|---|
| Comp. Ex. A | none | 88 | Poor |
| Comp. Ex. B | (EtO)$_3$Si-CH$_2$CH$_2$CH$_2$-NH-C(=O)-CH$_2$CH$_2$CH$_2$-OH | 95.3 | Poor |
| Comp. Ex. C | (EtO)$_3$Si-CH$_2$CH$_2$CH$_2$-N(CH$_2$CH$_2$OH)$_2$ | 94.5 | Poor |
| Comp. Ex. D | (EtO)$_3$Si-CH$_2$CH$_2$CH$_2$-NCO (ICPTES) | 89.2 | Poor |
| 3A | (EtO)$_3$Si-CH$_2$CH$_2$CH$_2$-NH-C(=O)-O-CH$_2$CH$_2$CH$_2$-OH (ICPTES-PDO) | 20.8 | Good |

TABLE 2-continued

| Sample | Silica Surface Treatment | Haze, % | Dispersion Quality by TEM |
|---|---|---|---|
| 3B | ICPTES-Polyol 3 (EtO)$_3$Si-CH$_2$CH$_2$CH$_2$-NH-C(O)-O-(CH$_2$)$_4$-(O-(CH$_2$)$_4$)$_n$-OH, n = 3 | 23.4 | Good |
| 3C | ICPTES-Polyol 7 (EtO)$_3$Si-CH$_2$CH$_2$CH$_2$-NH-C(O)-O-(CH$_2$)$_4$-(O-(CH$_2$)$_4$)$_n$-OH, n = 7 | 85.4 | Poor |
| 3D | ICPTMS-BDO | | Good |
| 3E | ICPTMS-n-propanol | 24.5 | Good |

Example 5

Polymerization of PBT in the Presence of SiO2 Surface Treated with ICPTES-BDO Dimethylterephthalate (110.86 g, 0.57 mol), 1,4-butanediol (BDO) (85.47 g, 0.95 mol) and 22.6% colloidal surface treated silica in PDO (surface treatment with ICPTES-BDO, 26.47 g) were charged to a 500 mL three necked round bottom flask. An overhead stirrer and a distillation condenser were attached. The reaction mass was kept under N$_2$ purge atmosphere. The contents were degassed three times by evacuating down to 500 mtorr and refilling back with N$_2$ gas. 145 µL of catalyst Tyzor® TnTBT was added under a N$_2$ blanket after the first evacuation. The flask was immersed in a preheated metal bath set at 160° C. The solids were allowed to melt completely at 160° C. and the stirrer speed was slowly increased to 180 rpm. The temperature was increased to 225° C. The system was maintained at 225° C. for 40 minutes to distill off most of the methanol. The temperature was increased to 250° C., the nitrogen flush was closed off and vacuum ramp was started. The reaction was maintained under vacuum for approximately 60 min. Analytical results: $M_n$=31300 g/mol, $M_w$=77400 g/mol, $T_g$=42° C., $T_m$=222° C., and $T_{HC}$=186° C. The inorganic silica content as determined by ash analysis was found to be 4.56 wt %. TEM indicated dispersion quality was excellent.

Example 6

Mechanical Properties of Silica/PPT Nanocomposites

Mechanical properties of samples prepared in Example A, Example B, Example C, Comparative Example A, Comparative Example B, and Comparative Example C were measured as described above and are presented in Table 3.

TABLE 3

| Example | Dispersion | Tensile Modulus (MPa) | Tensile Strength (MPa) | Elongation (%) | Flexural Modulus E (100° C.) MPa | Flexural Modulus E (205° C.) MPa |
|---|---|---|---|---|---|---|
| Comp. Ex. A | Poor | 2806.2 (85.6) | 48.1 (8.1) | 1.9 (0.4) | 512.6 | 343.0 |
| Comp. Ex. B | Poor | 2935.4 (163.3) | 31.4 (3.4) | 1.1 (0.1) | 356.1 | 202.3 |
| Comp. Ex. C | Poor | 2864.2 (74.1) | 29.5 (4.9) | 1.1 (0.2) | 388.8 | 335.9 |
| 3A | Good | 2784.6 (57.2) | 55.3 (2.9) | 2.3 (0.2) | 567.7 | 372.2 |
| 3B | Good | 2776.8 (61.4) | 49.5 (8.4) | 2.0 (0.4) | 408.5 | 303.5 |
| 3C | Poor | 2778.0 (133.1) | 41.2 (8.0) | 1.6 (0.4) | 422.5 | 278.4 |

Statistical Analysis

Tensile strength: A comparison of the combined data for the four samples with poor dispersion with the combined data for the two samples with good dispersion shows that there is a statistically significant difference between the two groups:

Two-Sample T Test for Poor Dispersion vs. Good Dispersion

| Dispersion | N | Mean Tensile Strength | StDev | SE Mean |
|---|---|---|---|---|
| Poor | 16 | 37.55 | 9.66 | 2.4 |
| Good | 8 | 52.37 | 6.57 | 2.3 |

Difference = mu (Poor dispersion) − mu (Good dispersion)
Estimate for difference: −14.82
95% CI for difference: (−21.83, −7.81)
T-Test of difference = 0 (vs. not =): T-Value = −4.42, DF = 19,
P-Value = 0.000

% Elongation: A comparison of the combined data for the four samples with poor dispersion with the combined data for the two samples with good dispersion shows that there is a statistically significant difference between the two groups:

Two-sample T test for Poor Dispersion vs. Good Dispersion

| Dispersion | N | Mean % Elongation | StDev | SE Mean |
|---|---|---|---|---|
| Poor | 16 | 1.418 | 0.457 | 0.11 |
| Good | 8 | 2.158 | 0.354 | 0.13 |

Difference = mu (Poor Dispersion) − mu (Good Dispersion)
Estimate for difference: −0.739
95% CI for difference: (−1.097, −0.382)
T-Test of difference = 0 (vs. not =): T-Value = −4.36, DF = 17,
P-Value = 0.000

Modulus: A comparison of the combined data for the four samples with poor dispersion with the combined data for the two samples with good dispersion shows that there is not a statistically significant difference in room temperature tensile modulus between the two groups (t-test P=0.089). A similar lack of statistical significance was found for flexural modulus by DMA at elevated temperatures.

What is claimed is:

1. A composition described by the structure of Formula (I)

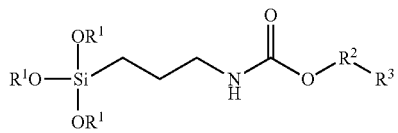

wherein each $R^1$ is independently a $C_{1-4}$ alkyl group; $R^2$ has a formula weight less than about 5000 and $R^2$ is a divalent alkylene group or a —$(CH_2)_{(3+3n)}O_n$— group,

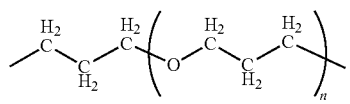

wherein n=0 to 85; and $R^3$ is OH.

2. The composition of claim 1 wherein $R^1$ is ethyl.
3. The composition of claim 2 wherein n=0 to 5.
4. An article of manufacture comprising the composition of claim 1.

* * * * *